United States Patent [19]

Nielsen

[11] Patent Number: 4,560,451
[45] Date of Patent: Dec. 24, 1985

[54] ELECTROLYTIC PROCESS FOR THE PRODUCTION OF ALKENE OXIDES

[75] Inventor: Kenneth A. Nielsen, Charleston, W. Va.

[73] Assignee: Union Carbide Corporation, Danbury, Conn.

[21] Appl. No.: 490,963

[22] Filed: May 2, 1983

[51] Int. Cl.$^4$ ............................................... C25B 3/02
[52] U.S. Cl. ........................................ 204/79; 204/80
[58] Field of Search ..................... 204/79, 80; 549/522, 549/521, 520

[56] References Cited

U.S. PATENT DOCUMENTS

| | | | |
|---|---|---|---|
| 2,237,284 | 4/1941 | Alquist | 549/522 |
| 3,000,909 | 9/1961 | Roberts | 549/522 |
| 3,635,803 | 1/1972 | Binns et al. | 204/80 |
| 3,894,059 | 7/1975 | Selvaratnam | 549/522 |
| 4,243,492 | 1/1981 | Yamamura | 549/522 |
| 4,270,995 | 6/1981 | Goodridge et al. | 204/72 |

Primary Examiner—John F. Niebling
Attorney, Agent, or Firm—Paul W. Leuzzi, II

[57] ABSTRACT

Alkene oxide can be made in a simple, closed process that uses electrolysis to make bromine and hydroxide from bromide and water. The alkene reacts with bromine and then water to form an alkene bromohydrin, which is dehydrobrominated by hydroxide, regenerating bromide, to give alkene oxide.

The main by-product in propylene oxide production is 1,2-dibromopropane, made by propylene reacting with bromine and then bromide. Since formation of 1,2-dibromopropane consumes propylene, electrical power, and bromide, which must be recovered, it is desirable to minimize its formation.

It has been discovered that adding carbonate and/or bicarbonate to the bromide electrolyte reduces the formation of 1,2-dibromopropane independently of any pH effect.

Carbonate/bicarbonate can be used to reduce formation of dibromo-compounds produced in epoxidation of other alkenes using the electrobromohydrin process.

Other carboxylic group and/or carboxylate-group materials, which are functionally similar to bicarbonate, can also reduce formation of dibromo-compounds, as demonstrated using ethylene diamine tetraacetic acid disodium salt to reduce formation of 1,2-dibromopropane in propylene oxide production.

16 Claims, No Drawings

ELECTROLYTIC PROCESS FOR THE PRODUCTION OF ALKENE OXIDES

BACKGROUND OF THE INVENTION

1. Field of the Invention

The present invention relates to a novel process for producing alkene oxide. More particularly, the present invention relates to the addition of carboxylic-group and/or carboxylate-group containing materials in the electrolysis of bromide, water, and alkenes during the production of alkene oxides.

2. Description of the Prior Art

Propylene oxide is a bulk commodity chemical used mainly to make polyols and polyethers for urethane polymers and to make propylene glycol for unsaturated polyester resins. But present manufacturing processes use raw materials inefficiently, produce large amounts of coproducts, produce a large waste and pollution burden, and/or use large amounts of energy.

The hydroperoxide coproduct processes are a common method of manufacturing propylene oxide and are exemplified by the tertiary butanol process. In this process, isobutane is oxidized by molecular oxygen to a tertiary butyl hydroperoxide, which thereafter reacts with propylene to form propylene oxide and tertiary butanol. One drawback to this process is that it produces an equal or greater amount of coproducts.

Another process is where hydrogen peroxide is reacted with recycled propionic acid to form perpropionic acid, which thereafter reacts with propylene to form propylene oxide. However, the high cost of hydrogen peroxide makes this process uneconomical in most circumstances.

Peracetic acid, produced by reacting acetaldehyde with ethyl acetate and air, can be used to epoxidize propylene but gives over one ton of coproduct acetic acid per ton of propylene oxide.

The direct oxidation of propylene by molecular oxygen to propylene oxide gives only 5–70% propylene efficiency and many undesirable byproducts. It should be noted that this route has never been commercialized.

The conventional process is the chlorohydrin process, wherein propylene reacts with chlorine in acidic water to form propylene chlorohydrin and 1,2-dichloropropane. Then, in a separate dehydrochlorination step, the chlorohydrin is contacted with a lime slurry to produce propylene oxide and calcium chloride. The major drawback to this process is that, for each ton of propylene oxide, 0.1 to 0.2 tons of propylene dichloride are produced, and typically 2 tons of calcium chloride in 43 tons of waste water must be disposed of.

To alleviate the chloride disposal problem, the conventional chlorohydrin process can be integrated with a dedicated conventional chlorine/caustic plant, but the NaCl brine leaving the chlorohydrin plan is too dilute to feed directly to chlorine cells. Since concentrating the brine is too expensive, after adding NaCl only part of it can be recycled to the dedicated chlorine plant; the remainder must be consumed in another large chlorine plant. Therefore propylene oxide and organic byproducts must be completely steam stripped from the brine, and this consumes an extraordinary amount of energy.

To eliminate brine loss and dependence on a second chlorine plant, total-NaCl brine-recycle processes have been proposed. These use conventional chlorine diaphragm or membrane cells but make propylene chlorohydrin by reacting propylene directly with the chlorine dissolved in the acidic anolyte. The anolyte is then mixed with a highly basic catholyte to swing the pH to convert the propylene chlorohydrin to propylene oxide and chloride. The efficiency is similar to the conventional process. After the products are removed, the total brine is recycled to the chlorine cell, after replacing chloride lost due to 1,2-dichloropropane and bis(chloropropyl) ether formations.

The in situ generation of propylene oxide using a chlorine cell has several disadvantages as well as the stated advantages. The cells must be operated at elevated temperature, typically 50°–60° C. This severely reduces propylene solubility and thus reduces the obtainable propylene oxide concentration, which also makes product recovery more difficult. Elevated temperature also increases propylene glycol formation by propylene oxide hydrolysis. Typically the cells must be operated at less than half the electrical current density of chlorine plants and this significantly increases the capital cost per unit of chlorine generated. Furthermore, the in situ generation of propylene oxide does not work at all in an undivided cell, because rapid formations of propylene chlorohydrin and propylene oxide are not compatible at any common pH. Chlorate formation is also prohibitive in an undivided cell. Therefore a membrane or diaphragm is needed, but since these materials are costly, divided cells can be expensive to build, the capital costs being very high. A membrane or diaphragm can significantly increase the voltage drop across a cell and hence increase the electrical power consumption. Also, the very large pH gradient across the diaphragm or membrane promotes fouling when organics are in the brine. Formation of a separate 1,2-dichloropropane phase must be avoided because both chlorine and propylene dissolve into it and form more 1,2-dichloropropane selectively.

Bromide electrolysis avoids the disadvantages of a chlorine-based system. Propylene oxide can be made in a simple, closed process that uses electrolysis to make bromine from bromide at the anode and hydroxide (and hydrogen) from water at the cathode. Propylene reacts with bromine and then water to form propylene bromohydrin, which is dehydrobrominated by hydroxide, regenerating the bromide, to give propylene oxide. The main byproduct is 1,2-dibromopropane and a minor amount of propylene glycol forms. Between pH 8 and 11, propylene bromohydrin and propylene oxide form rapidly at the same pH. Therefore a diaphragm or membrane is not needed and all reactions can occur within the undivided reactor. This simplifies reactor design and considerably lowers reactor capital costs. The lower electrolysis voltage of bromine and the absence of a diaphragm or membrane reduce the voltage drop across the cell and hence reduce electrical power consumption. Because bromine is more reactive than chlorine, reaction with propylene is rapid at and below room temperature. Operating at lower temperatures increases the propylene solubility which in turn increases propylene oxide concentration, all of which helps product recovery. Formation of 1,2-dibromopropane within any 1,2-dibromopropane phase present is insignificant because the free-bromine concentration is very low. Therefore, the reactor can be operated with an electrolyte saturated in 1,2-dibromopropane, which can then be removed easily by settling. Propylene efficiency is similar to conventional chlorine-based systems.

It has now been discovered that by adding carbonate and/or bicarbonate to the bromide electrolyte, the formation of 1,2-dibromopropane is effectively reduced in making propylene oxide in situ using bromide electrolysis in an undivided reactor. This occurs independently of any pH effect (carbonate and bicarbonate form a buffer, which is desirable to control pH in industrial scale reactors).

SUMMARY OF PRIOR ART

The basic electrohalohydrin propylene oxide process patent, U.S. Pat. No. 3,288,692, was issued in 1966 to Joseph A. M. LeDuc and assigned to Pullman Incorporated. The patent defines a process where an aqueous medium containing a metal halide is electrolyzed with the addition of an olefin to produce olefin oxide. During electrolysis the halide is oxidized at the anode to generate free halogen, which reacts with the olefin and water to form a halohydrin derivative. Water is electrolyzed at the cathode to produce hydroxide and hydrogen. The halohydrin reacts with the hydroxide to form olefin oxide, all within the cell.

The patent specifies that the metal halide may be any water-soluble compound having a water-soluble metal hydroxide, or a mixture of such salts, in concentrations varying from dilute to saturated. The examples illustrate only chloride electrolysis. The cell may be operated at nearly any temperature or pressure provided the electrolyte remains liquid. Although the patent fails to specify any specific anode or cathode materials, the discussion states that the anode may be graphite, platinum, magnetite, or an inert substrate such as polyethylene or teflon metallized with copper, silver, or platinum. The cathode may be any conductive material chemically inert to caustic and is usually steel or stainless steel. Porous anodes may be used to feed the olefin. The patent teaches cells with or without a diaphragm. (Strictly speaking, the chloride process can be used in an undivided cell if precautions are taken to prevent active mixing of the anolyte and catholyte so as to preserve a pH gradient across the cell, and this is illustrated in two examples. However, this is an impractical limitation and the reported performance is very poor. All other examples use a diaphragm.) Various cell configurations are described. The examples illustrate epoxidation of ethylene and propylene.

Later electrochlorohydrin process improvement patents focus on diaphragm materials, anode materials, using a membrane instead of a diaphragm, cell design, and prevention of fouling.

A variation patented by Lummus (U.S. Pat. Nos. 4,008,133 and 4,126,526) reacts the chlorine with tert-butanol to form tert-butyl hypochlorite, which is recovered and thereafter reacted with propylene and chloride-free water to form the propylene chlorohydrin.

Other patents citing bromide electrolysis (electrobromohydrin process) address particular undivided cell designs as does much of the published papers on the electrobromohydrin process. (See U.S. Pat. No. 3,394,059, British Pat. No. 1,504,690, German Offen No. 2,336,288 and WO. No. 79-00323.)

None of the above patents or studies teach or suggest the use of carbonate and/or bicarbonate or carbon dioxide in any way. Since the present invention does not concern anode, cathode, diaphragm, or membrane materials, fouling, or cell design, other than being directed towards an undivided cell, the above improvement patents and studies merely document the known literature.

U.S. Pat. No. 3,894,059, issued in 1975 to T. Selveratnam and assigned to Petrocarbon Developments Limited, uses carbon dioxide absorption and desorption caused by swinging electrolyte temperature to swing the pH, presumably instead of using a divided cell (the electrolysis method is not described). The process is divided into three major parts: (1) an NaCl solution is electrolyzed to produce a solution containing 2-5 wt % sodium hypochlorite, NaOCl, (2) equal molar propylene and carbon dioxide are absorbed into the NaOCl solution at less than 10° C. to form an equal molar solution of bicarbonate and propylene chlorohydrin, and (3) this solution is heated to 50°-115° C. to convert the chlorohydrin to propylene oxide and the bicarbonate to carbon dioxide, which is recycled. The patent fails to describe 1,2-dichloropropane (propylene dichloride) formation or how the carbon dioxide absorption affected the amount of this formed.

A 1978 paper by Kerti, Kovacs, Siska, and Zold, (Periodica Polytechnica, Chemical Engineering 22: 73-79) describes a propylene oxide process very similar to the one described in U.S. Pat. No. 3,894,059 insofar as carbon dioxide absorption and desorption is caused by a temperature change used to swing the pH and hence transform propylene chlorohydrin to propylene oxide, all the while using an undivided electrolysis reactor. However, the paper lacks experimental information and particularly information on 1,2-dichloropropane formation or how the carbon dioxide absorption affected the amount of this bi-product formed.

These carbon dioxide absorption/desorption processes differ fundamentally from the present disclosure in that (1) they use chlorine instead of bromine; (2) the propylene chlorohydrin and propylene oxide are produced in separate reactors external to the electrolysis reactor rather than having all reactions occurring in situ in the electrolysis reactor; (3) carbon dioxide is being absorbed and desorbed instead of maintaining a relatively constant carbonate and/or bicarbonate concentration; (4) a temperature change of the electrolyte stream is used instead of relatively isothermal processing; and (5) a pH swing of the electrolyte stream is used instead of constant pH.

SUMMARY OF THE INVENTION

The present invention provides a novel process for producing alkene oxide, and more particularly propylene oxide. This novel process comprises adding carbonate and/or bicarbonate or some other carbonate generating material to the bromide electrolyte in a electrobromohydrin process. The object of this addition is to reduce the formation of the 1,2-dibromopropane byproduct.

The reduction in 1,2-dibromopropane formation caused by the present invention is beneficial because it accomplishes the following additional objects of the present invention:

(1) it increases the propylene efficiency to propylene oxide;

(2) it reduces the electrical power needlessly consumed by the production of 1,2-dibromopropane;

(3) it reduces excess cathodic hydroxide not consumed because 1,2-dibromopropane forms instead of propylene oxide, this in turn reduces the pH rise in the reactor and makes the pH easier to control;

(4) it reduces the amount of 1,2-dibromopropane that must be recovered from the electrolyte;

(5) it reduces the amount of 1,2-dibromopropane that must be processed to recover bromide to recycle back to the electrolyte in order to maintain bromide inventory; and (6) it reduces the electrical resistance of the electrolyte caused by dispersion of nonconducting 1,2-dibromopropane droplets; this lowers voltage drop and electrical power consumption.

Additionally, it is an object of the invention to provide a process which does not require a divided reactor.

DETAILED DESCRIPTION OF THE INVENTION

In the electrobromohydrin process for propylene oxide using an undivided electrolysis reactor, bromide is oxidized at the anode to molecular bromine, and water is reduced at the cathode to hydroxide and hydrogen gas.

$$2\ Br^- \rightarrow Br_2 + 2e^-$$
$$2\ H_2O + 2e^- \rightarrow H_2 + 2OH^-$$
$$\overline{2\ Br^- + 2H_2O \rightarrow Br_2 + 2OH^- + H_2}$$

The bromine reacts with dissolved propylene to form a reactive cyclic propylene bromonium cation intermediate and a free bromide anion.

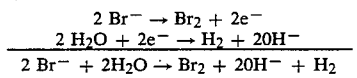

The product distribution is determined by (1) the relative reactivity of the propylene bromonium cation towards different nucleophiles and (2) the concentrations of the nucleophiles. In the normal electrobromohydrin process the product distribution is determined by the bromide concentration, since water, being the preferred solvent, has constant concentration. Propylene bromonium reacts with water to form propylene bromohydrin

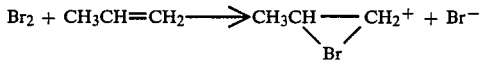

and reacts with bromide to form 1,2-dibromopropane.

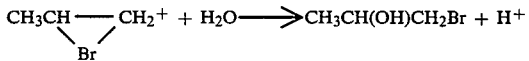

Since water is present in high concentration, propylene bromohydrin is the primary product. However, propylene bromonium is more reactive towards bromide, so although the concentration of bromide is much less, an appreciable amount of 1,2-dibromopropane forms. Propylene bromohydrin reacts with the hydroxide formed at the cathode to give propylene oxide and regenerate bromide.

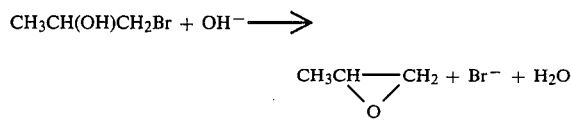

The net reaction is propylene plus water going to propylene oxide plus hydrogen.

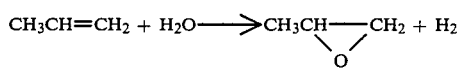

Propylene bromonium is believed to react with carboxylic-group and/or carboxylate-group containing material, such as carbonate or bicarbonate, to form a carbonic ether intermediate which is hydrolyzed rapidly by water or hydroxide to give propylene bromohydrin and regenerate the carboxylic-group and/or carboxylate-group containing material.

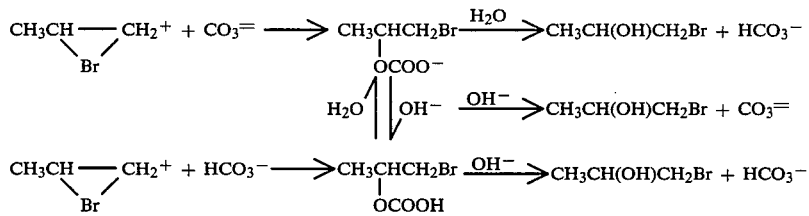

Therefore, by adding the carboxylic-group and/or carboxylate-group containing material to the bromide electrolyte, the free propylene bromium concentration available to react with bromide to form 1,2-dibromopropane is lowered and hence the formation of 1,2-dibromopropane is lowered while increasing the formation of propylene bromohydrin and propylene oxide.

In solution carbonate and bicarbonate exist in equilibrium and the relative amounts of each depends on the pH, more bicarbonate is present at low pH and more carbonate is present at high pH.

$$HCO_3^- + OH^- \rightleftharpoons CO_3^= + H_2O$$

If the reactivity of propylene bromonium is different towards carbonate and bicarbonate, at constant total carbonate plus bicarbonate concentration the catalytic rate of formation of propylene bromohydrin will vary with pH because of the variation in the relative amounts of carbonate and bicarbonate.

The present invention is independent of the method of forming or introducing the carbonate and/or bicarbonate into the electrolyte provided the resulting cations are inert, are largely dissociated from the carbonate and bicarbonate in solution, are soluble, and have soluble hydroxides and bromides. The favored preparation is to add metal carbonate and metal bicarbonate in correct proportion to give the desired pH with the metal cation being the same as that for the bromide electrolyte. Carbonate generating materials include, but are not limited to, sodium carbonate, sodium bicarbonate, potassium carbonate, potassium bicarbonate, ammonium carbonate, ammonium bicarbonate, tetraalkylammonium carbonate, tetraalykylammonium bicarbonate, and carbonates and bicarbonates of lithium, rubidium, cesium, beryllium, magnesium, calcium, strontium, barium, cobalt, iron, nickel, copper, zinc, etc. Sodium carbonate, sodium bicarbonate, potassium carbonate, and potassium bicarbonate are preferred. The carbonate and bicarbonate may also be prepared in solution by dissolving carbon dioxide in the electrolyte, which forms carbonic acid by reaction with water, and adding a metal hydroxide, such as potassium hydroxide or sodium hydroxide, to neutralize the carbonic acid and adjust the pH to the desired level.

The present invention should have effect over the broad range of total concentrations of carboxylic-group and/or carboxylate-group containing materials of from 0.001 molar to their solubility limit, but the favored total concentration range is 0.01 to 0.5 molar.

The present invention should also have effect over the range of pH 3 to 12, but the range of pH 5 to 11 is preferred. In an undivided reactor the range of pH 8 to 11 is preferred.

The present invention is also independent of the method of forming or introducing the bromide electrolyte into the aqueous solvent provided the resulting cations are inert, are largely dissociated from the carbonate and bicarbonate in solution, are soluble, and have soluble hydroxides. Potassium bromide and sodium bromide are favored electrolytes, however, other known electrolytes are also useful, such as ammonium bromide, tetralkylammonium bromide, lithium bromide, rubidium bromide, cesium bromide, beryllium bromide, magnesium bromide, calcium bromide, strontium bromide, barium bromide, cobalt bromide, nickel bromide, copper bromide, zinc bromide, and the like. The invention should have effect over a bromide concentration ranging from very dilute to the solubility limit but it is more effective at low bromide concentrations. The favored bromide concentration range is 0.05 to 0.5 molar. Although the invention is effective below 0.05 molar bromide, such low bromide concentrations are not practical because they severely limit the electrical current density at which the reactor can be operated.

The present invention can be used with or without inert supporting electrolyte(s) added to increase solution conductivity, in addition to the carbonate and bicarbonate, which also function as supporting electrolytes. Such supporting electrolytes include potassium sulfate, sodium sulfate, ammonium sulfate, tetraalkylammonium sulfate, calcium sulfate, magnesium sulfate, potassium phosphate, sodium phosphate, ammonium phosphate, tetraalkylammonium phosphate, calcium phosphate, magnesium phosphate, potassium nitrate, sodium nitrate, ammonium nitrate, tetraalkylammonium nitrate, calcium nitrate, magnesium nitrate, potassium bromate, sodium bromate, potassium chlorate, sodium chlorate, etc. Potassium sulfate, sodium sulfate, potassium bromate, and sodium bromate are preferred.

The present invention should have effect over ranges of temperature and pressure that maintain the aqueous solvent liquid and do not thermally decompose the carbonate and bicarbonate to any significant degree. Lower temperatures are favored, in particular in the range of 0° C. to 40° C., since lower temperatures increase the propylene solubility in the aqueous solvent. Atmospheric or higher propylene pressure is favored since higher propylene pressure increases propylene solubility.

Any suitable bromide electrolysis anode material or construction can be employed. Examples include, but are not limited to, graphite, platinized titanium, ruthenized titanium, dimensionally stable anodes developed for chloride electrolysis by the chlor/alkali industry, lead dioxide, manganese dioxide, platinum-metal oxides alone and in mixtures with other metal oxides, such as a mixture of ruthenium, tin, and titanium oxides, and transition metal oxides alone and in mixtures with other metal oxides, such as cobalt spinel oxide and bimetal cobalt spinel oxide containing zinc, magnesium, copper, or zirconium. A ruthenized titanium anode consisting of a coating containing primarily ruthenium, tin, and titanium oxides, such as used commercially for chloride electrolysis, is preferred.

Additionally, any suitable hydroxide generating cathode material or construction can be used. Examples include graphite, steel, stainless steel, nickel, platinum, copper, titanium, zinc, iron, lead, silver, cadmium, palladium, mercury, and materials stable in bromide solution while protected by a cathodic voltage. A cathode of solid or porous nickel is preferred.

Although the present invention is independent of electrolytic reactor design, an undivided reactor, i.e. one without a diaphragm or membrane, is preferred.

The present invention is independent of the anode and cathode electrical current densities used, but anode and cathode current densities in the range of 1 to 20 amperes/square-decimeter are favored.

The present invention is not limited to those reactions between bromine and propylene dissolved in water which are carried out within an electrolytic reactor, but may also be conducted external to the reactor generating the bromine. For instance, an undivided electrolytic reactor may generate a solution containing bromine and hydroxide in water with no propylene present. If this solution is reacted with propylene in a separate reactor, adding carboxylic-group and/or carboxylate-group containing material to the solution will reduce the formation of 1,2-dibromopropane since the same reactions are involved as would occur within the electrolytic reactor. In aqueous solution, bromine exists in very rapid equilibrium with hypobromous acid, HOBr, hypobromite, OBr$^-$, and tribromide, Br$_3^-$.

| Acidic Solution | Basic Solution |
|---|---|
| $Br_2 + H_2O \rightleftharpoons H^+ + Br^- + HOBr$ | $Br_2 + 2OH^- \rightleftharpoons Br^- + OBr^- + H_2O$ |
| $HOBr \rightleftharpoons H^+ + OBr^-$ | $HOBr + OH^- \rightleftharpoons OBr^- + H_2O$ |
| $Br_2 + Br^- \rightleftharpoons Br_3^-$ | $Br_2 + Br^- \rightleftharpoons Br_3^-$ |

The equilibrium mole fractions of the species are determined by the local pH and bromide concentration. Bromine and tribromide dominate below pH 7.4, hypobromous acid is dominant for pH in the range of 7.4 to 8.7, and hypobromite dominates above pH 8.7. But molecular bromine is the only species which reacts rapidly with propylene and some bromine is always present to carry out the reaction even if the other bromine species predominate. Therefore, the present invention envisions the use of any bromine-evolving material as useful in its process. In the case of an undivided reactor with no propylene present, this produces a solution that is predominately hypobromite or hypobromous acid. But contacting this solution with propylene in a second reactor eventually causes all hypobromite, hypobromous acid, and tribromide to convert to bromine and be reacted out of solution by the propylene. However, reacting the bromine with propylene within the electrolytic reactor is favored because hypobromous acid and hypobromite irreversibly disproportionate to bromate when present in appreciable concentration.

It is conceivable that a bromine solution can be generated as the anolyte of a membrane or diaphragm reactor and then reacted with propylene in a separate reactor to generate propylene bromohydrin and 1,2-dibromopropane, and this mixture then mixed with the basic catholyte to convert the propylene bromohydrin to propylene oxide, but this mode of operation is not favored, although the benefits of the present invention should apply.

Carboxylic-group and/or carboxylate-group containing materials are effective in reducing formation of 1,2-dibromopropane even when bromide is not present initially in the reaction solution. Molecular bromine can be generated in the anolyte of a membrane or diaphragm reactor and then recovered from solution as pure bromine or pure bromine can be manufactured by oxidizing bromide using molecular chlorine. The reaction of bromine with propylene dissolved in bromide-free water generates 1,2-dibromopropane in addition to propylene bromohydrin because of the bromide generated in forming propylene bromonium, although the amount formed is less than if bromide were added. Thus, with the addition of a carboxylic-group and/or carboxylate-group containing material, without there occurring electrolysis, the formation of 1,2-dibromopropane is decreased. This occurs before the addition of the base to convert the propylene bromohydrin to propylene oxide.

Water is an essential reactant and cannot be eliminated from the process since it is necessary for generating hydroxide at the cathode and for reaction with propylene bromonium to form propylene bromohydrin. Therefore a water-free solvent can not be used, although water and a cosolvent can be.

The use of an inert cosolvent with water, such as methyl acetate, ethyl formate, 1,4-dioxane, 2-butanone, tetrahydrofuran, 1,2-ethanediol dimethyl ether, acetone, glycol diacetate, and 2,4-pentanedione, acts to increase propylene solubility and is also contemplated. Ether cosolvents are preferred, in particular 1,4-dioxane and tetrahydrofuran. Alcohols can be used as cosolvent but their use is not preferred because of potential reaction with the alkene oxide. A low proportion of cosolvent has minimal effect on propylene solubility while a high proportion of cosolvent adversely lowers the concentration of water, which may hurt reaction selectivity. Therefore a cosolvent concentration of 10 to 30 weight % is favored, although other concentrations may be employed.

The use of carboxylic-group and/or carboxylate-group containing materials can theoretically be used to reduce the formation of dibromo-compounds produced as a byproduct in the epoxidation of alkenes other than propylene using the electrobromohydrin process. This has been demonstrated by the epoxidation of 1-butene. Although the chemistry or mechanism is analogous for other alkene epoxidations, the effectiveness of using carbonate/bicarbonate will depend on the relative reactivity of the alkene bromonium cation intermediate towards bromide, carbonate, and bicarbonate. Such alkenes include, but are not limited to, substituted and unsubstituted acyclic and cyclic monoalkenes and polyalkenes, including straight and branched alkenes, as well as alkenes in which the double bond is in a terminal or nonterminal position or within a cyclic ring, such as ethylene, 1-butene, 2-butene, isobutene, 1-pentene, 2-pentene, isopentene, 3-ethyl-1-pentene, 1-hexene, 2-hexene, etc., cyclopentene, cyclohexene, 3-methyl-1-cyclohexene, etc., styrene, stilbene, 3-phenylpropylene, allyl chloride, allyl alcohol, butadiene, 2,3-dimethylbutadiene, 1,4-pentadiene, etc. (There is no preferred alkene because this depends upon the desired product; propylene for propylene oxide, ethylene for ethylene oxide, styrene for styrene oxide, etc.)

The alkene may be soluble in the electrolyte, have low solubility, or be insoluble and be supplied as a dispersion of gaseous bubbles, as a liquid emulsion, or as a solid suspension in the electrolyte or be dissolved in a gaseous, liquid, or solid carrier which is dispersed, emulsified, or suspended in the electrolyte.

An extractant may be used as an emulsion with the electrolyte or a stripping gas as a dispersion in the electrolyte or an adsorbent as a suspension in the electrolyte to facilitate recovery of the alkene oxide.

Carboxylic-group and/or carboxylate-group containing materials capable of forming ether linkages with an alkene bromonium cation, with the linkage capable of being hydrolyzed subsequently to give the alkene bromohydrin, can theoretically also be used to reduce formation of the corresponding dibromo-compounds in epoxidation by the electrobromohydrin process.

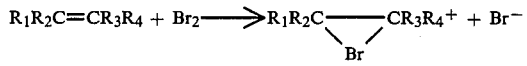

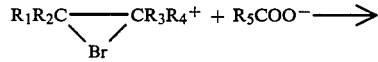

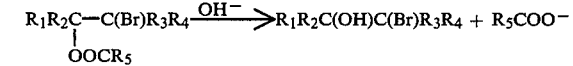

This has been demonstrated using ethylene tetraacetic acid disodium salt (EDTA disodium salt), which has functional carboxylic groups and/or carboxylate-group similar to bicarbonate, to reduce 1,2-dibromopropane formation in propylene oxide production.

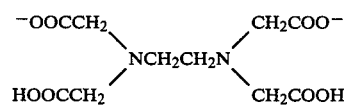

Other such carboxylic group and/or carboxylate-group containing materials may include, but are not limited to, carboxylic acids and salts, such as sodium formate, potassium formate, ammonium formate, sodium acetate, potassium acetate, ammonium acetate, calcium acetate, sodium propionate, potassium propionate, ammonium propionate, sodium benzoate, potassium benzoate, ammonium benzoate, phthalic acid disodium salt, phtalic acid monosodium salt, phthalic acid dipotassium salt, phthalic acid monopotassium salt, nitrilotriacetic acid disodium salt, nitrilotriacetic acid dipotassium salt, formic acid, acetic acid, propionic acid, phthalic acid and the like.

Whereas the exact scope of the instant invention is set forth in the appended claims, the following specific examples illustrate certain aspects of the present invention and, more particularly, point out methods of evaluating the same. However, the examples are set forth for illustration only and are not to be construed as limitations on the present invention except as set forth in the appended claims. All parts and percentages are by weight unless otherwise specified.

EXAMPLES

EXAMPLE 1

The electrolysis was done in an undivided reactor (no diaphragm or membrane) having a single pair of parallel vertical monopolar electrodes spaced 1 millimeter apart with 1.40 square-decimeters of electrolysis area (each) and a 12-inch electrolyte flow path. The anode is ruthenized titanium and the cathode is a solid nickel plate. Electrolyte circulates between the reactor and a packed column, where propylene absorption, propylene oxide and propylene dibromide stripping, and hydrogen bubble separation occur. The average flow velocity in the reactor is 3.8 ft/sec. The pH of the reactor feed is held constant by adding hydrobromic acid, which also stoichiometrically replaces bromide lost due to propylene dibromide formation and replaces water lost by electrolysis, reaction, and evaporation. The unit operates at steady state at atmospheric propylene pressure. Experimental runs are 22 hours.

At 30° C., average pH 10, 0.2 molar potassium bromide electrolyte, and 5.0 amperes/square-decimeter electrical current density, the average propylene consumption by 1,2-dibromopropane formation for two runs without carbonate/bicarbonate averaged 10.5 mole % whereas a run with 0.05 molar sodium carbonate and 0.05 molar sodium bicarbonate added gave a 1,2-dibromopropane formation of 6.2 mole %, for an average reduction in 1,2-dibromopropane formation of 41%.

EXAMPLE 2

Using the same equipment and procedure as in Example 1, at 30° C., average pH 10, 0.2 molar potassium bromide electrolyte, and 9.3 amperes/square-decimeter electrical current density, the average propylene consumption by 1,2-dibromopropane formation for two runs without carbonate/bicarbonate averaged 11.6 mole % whereas a run with 0.05 molar sodium carbonate and 0.05 molar sodium bicarbonate added gave a 1,2-dibromopropane formation of 7.3 mole %, for an average reduction in 1,2-dibromopropane formation of 37%.

EXAMPLE 3

Using the same equipment and procedure as in Example 1, at 30° C., average pH 10, 0.1 molar potassium bromide electrolyte, and 5.0 amperes/square-decimeter electrical current density, the average propylene consumption by 1,2-dibromopropane formation for a run without carbonate/bicarbonate but with 0.4 molar potassium sulfate inert supporting electrolyte added was 9.3 mole % whereas a run with, 0.05 molar sodium carbonate and 0.05 molar sodium bicarbonate added but with no supporting electrolyte gave a 1,2-dibromopropane formation of 4.6 mole %, for an average reduction in 1,2-dibromopropane formation of 50%.

EXAMPLE 4

Using the same equipment and procedure as in Example 1, at 30° C., average pH 10, 0.1 molar potassium bromide electrolyte, and 9.3 amperes/square-decimeter electrical current density, the average propylene consumption by 1,2-dibromopropane formation for a run without carbonate/bicarbonate but with 0.4 molar potassium sulfate inert supporting electrolyte added was 6.9 mole % whereas a run with 0.05 molar sodium carbonate and 0.05 molar sodium bicarbonate added but with no supporting electrolyte gave a 1,2-dibromopropane formation of 4.9 mole %, for an average reduction in 1,2-dibromopropane formation of 29%. However, these two runs were made under unfavorable conditions because the limiting electrical current density for bromine formation was exceeded and substantial amounts of molecular oxygen were formed by water electrolysis at the anode.

EXAMPLE 5

Using the same equipment and procedure as in Example 1, 1-butene was epoxidized instead of propylene to give 1,2-epoxybutane. At 20° C., average pH 10, 0.2 molar potassium bromide electrolyte, and 5.0 amperes/square-decimeter electrical current density, the average 1-butene consumption by 1,2-dibromobutane formation for a run without carbonate/bicarbonate was 15.9 mole % whereas a run with 0.025 molar sodium carbonate and 0.025 molar sodium bicarbonate added gave a 1,2-dibromobutane formation of 13.6 mole %, for a reduction in 1,2-dibromobutane formation of 14.5%.

EXAMPLE 6

Propylene oxide was made at room temperature and pressure by mixing 20 milliliters of 0.039 molar bromine (1 milliliter pure bromine dissolved in 500 milliliters water) into 100 milliliters of propylene-saturated solutions of (1) distilled water, which gave a propylene consumption by 1,2-dibromopropane formation of 5.2 mole %, and (2) distilled water with 0.05 molar sodium carbonate and 0.05 molar sodium bicarbonate added, which gave a 1,2-dibromopropane formation of 1.1 mole %, for a reduction in 1,2-dibromopropane formation of 79%.

EXAMPLE 7

Propylene oxide was made at room temperature and pressure by mixing 20 milliliters of 0.039 molar bromine (1 milliliter pure bromine dissolved in 500 milliliters water) into 100 milliliters of propylene-saturated solutions of (1) 0.1 molar potassium bromide, which gave a propylene consumption by 1,2-dibromopropane formation of 8.3 mole %, and (2) 0.1 molar potassium bromide with 0.05 molar sodium carbonate and 0.05 molar sodium bicarbonate added, which gave a 1,2-dibromopropane formation of 6.0 mole %, for a reduction in 1,2-dibromopropane formation of 28%.

EXAMPLE 8

Propylene oxide was made at room temperature and pressure by mixing 20 milliliters of 0.039 molar bromine (1 milliliter pure bromine dissolved in 500 milliliters water) into 100 milliliters of propylene-saturated solutions of (1) 0.2 molar potassium bromide, which gave a propylene consumption by 1,2-dibromopropane formation of 11.5 mole %, and (2) 0.2 molar potassium bromide with 0.05 molar sodium carbonate and 0.05 molar sodium bicarbonate added, which gave a 1,2-dibromopropane formation of 9.5 mole %, for a reduction in 1,2-dibromopropane formation of 17%.

EXAMPLE 9

Propylene oxide was made at room temperature and pressure by mixing 20 milliliters of 0.039 molar bromine (1 milliliter pure bromine dissolved in 500 milliliters water) into 100 milliliters of proplene-saturated solutions of (1) 0.5 molar potassium bromide, which gave a propylene consumption by 1,2-dibromopropane formation of 20.1 mole %, and (2) 0.5 molar potassium bromide with 0.05 molar sodium carbonate and 0.05 molar sodium bicarbonate added, which gave a 1,2-dibromopropane formation of 16.3 mole %, for a reduction of 1,2-dibromopropane formation of 19%.

EXAMPLE 10

Propylene oxide was made at room temperature and pressure by mixing 10 milliliters of 0.065 molar bromine (1 milliliter pure bromine dissolved in 300 milliliters water) into 100 milliliters of propylene-saturated distilled-water solutions containing (1) no carbonate/bicarbonate and (2) 0.0125 molar sodium carbonate and 0.0125 molar sodium bicarbonate. The carbonate/bicarbonate reduced the propylene consumption by 1,2-dibromopropane formation by 45%.

EXAMPLE 11

Propylene oxide was made at room temperature and pressure by mixing 10 milliliters of 0.065 molar bromine (1 milliliter pure bromine dissolved in 300 milliliters water) into 100 milliliters of propylene-saturated distilled-water solutions containing (1) no carbonate/bicarbonate and (2) 0.025 molar sodium carbonate and 0.025 molar sodium bicarbonate. The carbonate/bicarbonate reduced the propylene consumption by 1,2-dibromopropane formation by 72%.

EXAMPLE 12

Propylene oxide was made at room temperature and pressure by mixing 10 milliliters of 0.065 molar bromine (1 milliliter pure bromine dissolved in 300 milliliters water) into 100 milliliters of propylene-saturated distilled-water solutions containing (1) no carbonate/bicarbonate and (2) 0.05 molar sodium carbonate and 0.05 molar sodium bicarbonate. The carbonate/bicarbonate reduced the propylene consumption by 1,2-dibromopropane formation by 84%.

EXAMPLE 13

Propylene oxide was made at room temperature and pressure by mixing 10 milliliters of 0.065 molar bromine (1 milliliter pure bromine dissolved in 300 milliliters water) into 100 milliliters of propylene-saturated distilled-water solutions containing (1) 0.1 molar ethylene diamine tetraacetic acid disodium salt (EDTA disodium salt) and (2) no EDTA disodium salt. The EDTA disodium salt reduced the propylene consumption by 1,2-dibromopropane formation by 15%.

I claim:

1. An improved epoxidation process for alkenes in an electrolytic cell having a cathode and an anode, which process comprises employing an aqueous solution containing a soluble bromide as an electrolyte, adding to the bromide electrolyte from about 0.01 to 0.5 molar concentration of a catalyst to reduce the formation of dibromoalkene where said catalyst is a carboxylic-group and/or a carboxylate-group containing material prior to impressing a voltage between the cathode and the anode, which voltage induces flow through the electrolyte, and adding to the electrolyte, either before, during or after inducing said current flow, an alkene while providing a temperature and pressure sufficient to maintain the electrolyte in liquid phase and not decompose the carboxylic-group and/or carboxylate-group containing material while epoxidation occurs.

2. The process of claim 1 wherein the carboxylic-group and/or carboxylate-group containing material is selected from the group consisting of carbonates, bicarbonates, carboxylic acids, and carboxylic salts.

3. The process of claim 2 wherein the carboxylic-group and/or carboxylate-group containing material is either sodium or potassium carbonate.

4. The process of claim 2 wherein the carboxylic-group and/or carboxylate-group containing material is either sodium or potassium bicarbonate.

5. The process of claim 1 wherein the electrolyte is either a potassium or sodium bromide aqueous solution.

6. The process of claim 1 wherein an inert supporting electrolyte is used in association with the soluble bromide.

7. The process of claim 6 wherein the inert supporting electrolyte is selected from the group consisting of sulfates, phosphates, nitrates, bromates and chlorates.

8. The process of claim 6 wherein the inert supporting electrolyte is either potassium sulfate or bromate.

9. The process of claim 6 wherein the inert supporting electrolyte is either sodium sulfate or bromate.

10. The process of claim 1 wherein the electrolytic cell is an undivided electrolytic cell.

11. The process of claim 1 wherein the alkene is propylene.

12. An improved epoxidation process for propylene in an undivided electrolytic cell having a cathode and an anode, which process comprises employing either a potassium bromide or sodium bromide aqueous solution as an electrolyte, adding to the electrolyte from about 0.01 to 0.5 molar concentration of a catalyst to reduce the formation of dibromoalkene where said catalyst is sodium or potassium carbonate and/or a sodium or potassium bicarbonate prior to impressing a voltage between the cathode and the anode which voltage induces current flow through the electrolyte and adding to the electrolyte either before, during or after said current flow propylene while providing a temperature and pressure sufficient to maintain the electrolyte in liquid phase and not decompose the carbonate or bicarbonate while epoxidation occurs.

13. The process of claim 12 wherein the anode is ruthenized titanium.

14. The process of claim 12 wherein the cathode is either solid or porous nickel.

15. The process of claim 12 wherein the epoxidation occurs at a temperature in the range of 0° to 40° C.

16. The process of claim 12 wherein the epoxidation occurs at a propylene pressure equal to or greater than atmospheric.

* * * * *